United States Patent [19]

Li

[11] Patent Number: 5,158,617
[45] Date of Patent: Oct. 27, 1992

[54] METHOD OF CLEANING USING HYDROCHLOROFLUOROCARBONS HAVING 3 TO 5 CARBON ATOMS

[75] Inventor: Chien C. Li, East Aurora, N.Y.

[73] Assignee: Allied-Signal Inc., Morris Township, Morris County

[21] Appl. No.: 687,342

[22] Filed: Apr. 18, 1991

[51] Int. Cl.$^5$ .............................. B08B 3/08
[52] U.S. Cl. ............................ 134/40; 252/162; 252/172; 252/364
[58] Field of Search ............... 134/40; 252/162, 172, 252/364

[56] References Cited

FOREIGN PATENT DOCUMENTS 0347924 12/1989 European Pat. Off. .

Primary Examiner—Theodore Morris
Assistant Examiner—Zeinab El-Arini
Attorney, Agent, or Firm—Melanie L. Brown; Jay P. Friedenson

[57] ABSTRACT

A method of cleaning a surface of a substrate is provided. The solvent is selected from a group consisting of hydrochlorofluorocarbons having 3 to 5 carbon atoms and a maximum of two chlorine atoms. The environmental lifetime of the solvent is expected to be less than one year.

20 Claims, No Drawings

METHOD OF CLEANING USING HYDROCHLOROFLUOROCARBONS HAVING 3 TO 5 CARBON ATOMS

BACKGROUND OF THE INVENTION

The present invention relates to a method of cleaning a surface of a substrate using hydrochlorofluorocarbons having 3 to 5 carbon atoms.

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room-temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For soils which are difficult to remove, where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-described operations are well known in the art. For example, Sherliker et al. in U.S. Pat. No. 3,085,918 disclose such suitable vapor degreasers comprising a boiling sump, a clean sump, a water separator, and other ancilliary equipment.

Cold cleaning is another application where a number of solvents are used. In most cold cleaning applications, the soiled part is either immersed in the fluid or wiped with rags or similar objects soaked in solvents.

In cold cleaning applications, the use of the aerosol packaging concept has long been found to be a convenient and cost effective means of dispensing solvents. Aerosol products utilize a propellant gas or mixture of propellant gases, preferably in a liquified gas rather than a compressed gas state, to generate sufficient pressure to expel the active ingredients, i.e. product concentrates such as solvents, from the container upon opening of the aerosol valve. The propellants may be in direct contact with the solvent, as in most conventional aerosol systems, or may be isolated from the solvent, as in barrier-type aerosol systems.

Chlorofluorocarbon solvents, such as trichlorotrifluoroethane, have attained widespread use in recent years as effective, nontoxic, and nonflammable agents useful in degreasing applications and other solvent cleaning applications. Trichlorotrifluoroethane has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like. Trichlorotrifluoroethane has two isomers: 1,1,2-trichloro-1,2,2-trifluoroethane (known in the art as CFC-113) and 1,1,1-trichloro-2,2,2-trifluoroethane (known in the art as CFC-113a). CFC-113 has a boiling point of about 47° C. and has been found to have satisfactory solvent power for greases, oils, waxes, and the like.

Another commonly used solvent is chloroform (known in the art as HCC-20) which has a boiling point of about 63° C. Perchloroethylene is a commonly used dry cleaning and vapor degreasing solvent which has a boiling point of about 121° C. These compounds are disadvantageous for use as solvents because they are toxic; also, chloroform causes liver damage when inhaled in excess.

Although chlorine is known to contribute to the solvency capability of a compound, fully halogenated chlorofluorocarbons and hydrochlorofluorocarbons are suspected of causing environmental problems in connection with the earth's protective ozone layer. Thus, the art is seeking new compounds which do not contribute to environmental problems but yet provide the solvency properties of CFC-113.

Chlorofluorocarbons (CFCs) such as CFC-113 are suspected of causing environmental problems in connection with the ozone layer. Under the Clean Air Act, CFC-113 is being phased-out of production.

In response to the need for stratospherically safe materials, substitutes have been developed and continue to be developed. *Research Disclosure* 14623 (June 1978) reports that 1,1-dichloro-2,2,2-trifluoroethane (known in the art as HCFC-123) is a useful solvent for degreasing and defluxing substrates. In the EPA "Findings of the Chlorofluorocarbon Chemical Substitutes International Committee", EPA-600/9-88-009 (April 1988), it was reported that HCFC-123 and 1,1-dichloro-1-fluoroethane (known in the art as HCFC-141b) have potential as replacements for CFC-113 as cleaning agents.

Commonly assigned U.S. Pat. No. 4,947,881 teaches a method of cleaning using hydrochlorofluoropropanes having 2 chlorine atoms and a difluoromethylene group. European Publication 347,924 published Dec. 27, 1989 teaches hydrochlorofluoropropanes having a difluoromethylene group. International Publication Number WO 90/08814 published Aug. 9, 1990 teaches azeotropes having at least one hydrochlorofluoropropane having a difluoromethylene group.

A wide variety of consumer parts is produced on an annual basis in the United States and abroad. Many of these parts have to be cleaned during various manufacturing stages in order to remove undesirable contaminants. These parts are produced in large quantities and as a result, substantial quantities of solvents are used to clean them. It is apparent that the solvent used must be compatible with the material to be cleaned.

Other advantages of the invention will become apparent from the following description.

SUMMARY OF THE INVENTION

The present invention provides a method of cleaning a surface of a substrate which comprises treating the surface with a solvent which is a straight chain or branched hydrochlorofluorocarbon having 3 to 5 carbon atoms. The straight chain hydrochlorofluorocarbons having 3 carbon atoms are listed in Table I below.

TABLE I

| Number | Chemical Formula |
| --- | --- |
| HCFC-234ab | $CFH_2CCl_2CF_3$ |
| HCFC-234bb | $CF_3CFClCClH_2$ |
| HCFC-234bc | $CFH_2CFClCF_2Cl$ |
| HCFC-234fa | $CF_2ClCH_2CF_2Cl$ |
| HCFC-234fb | $CF_3CH_2CFCl_2$ |
| HCFC-243ec | $CF_2ClCFHCClH_2$ |
| HCFC-244ba | $CFH_2CFClCF_2H$ |
| HCFC-244da | $CF_2HCClHCF_2H$ |
| HCFC-244ea | $CF_2HCFHCFClH$ |
| HCFC-244ec | $CFH_2CFHCF_2Cl$ |
| HCFC-244fa | $CFClHCH_2CF_3$ |
| HCFC-244fb | $CF_2HCH_2CF_2Cl$ |
| HCFC-252dc | $CH_3CClHCF_2Cl$ |
| HCFC-253bb | $CH_3CFClCF_2H$ |
| HCFC-253ea | $CF_2HCFHCClH_2$ |
| HCFC-253ec | $CH_3CFHCF_2Cl$ |
| HCFC-253fa | $CF_2HCH_2CFClH$ |
| HCFC-253fc | $CFH_2CH_2CF_2Cl$ |
| HCFC-262fa | $CF_2HCH_2CClH_2$ |
| HCFC-271b | $CH_3CFClCH_3$ |
| HCFC-271fb | $CH_3CH_2CFClH$ |

Known methods for making fluorinated compounds can be modified in order to form the straight chain hydrochlorofluorocarbons having 3 carbon atoms of the present invention.

For example, Haszeldine, *Nature* 165, 152 (1950) teaches the reaction of trifluoroiodomethane and acetylene to prepare 3,3,3-trifluoro-1-iodopropene which is then dehydroiodinated to form 3,3,3-trifluoropropyne. By using 3,3,3-trifluoropropyne as a starting material, $CF_3CFClCClH_2$ (HCFC-234bb) may be prepared as follows. Commercially available trifluoromethyl iodide may be reacted with acetylene to prepare 3,3,3-trifluoro-1-iodopropene which is then dehydroiodinated to form 3,3,3-trifluoropropyne. The 3,3,3-trifluoropropyne may then be reacted with commercially available hydrogen fluoride to form 2,3,3,3-tetrafluoro-1-propene which is then chlorinated to form 1,2-dichloro-2,3,3,3-tetrafluoropropane.

E. T. McBee et al., "Fluorinated Derivatives of Propane", *J. of Amer. Chem Soc.* 69, 944 (1947) teach a method for the preparation of $CClF_2CHClCH_3$ (HCFC-252dc). Commercially available 1,1-dichloropropene is reacted with commercially available commercially available hydrogen chloride to form 1,1,1-trichloropropane. The 1,1,1-trichloropropane is then reacted with commercially available hydrogen fluoride to form 1-chloro-1,1-difluoropropane which is then chlorinated to form 1,2-dichloro-1,1-difluoropropane.

$CF_2ClCFHCClH_2$ (HCFC-243ec) may be prepared as follows. Commercially available 1,1,3-trichloropropene may be dehydrohalogenated to form 1,3-dichloro-1-propyne. The 1,3-dichloro-1-propyne may then be fluorinated to form 1,3-dichloro-1,2-difluoro-1-propene which may then be reacted with commercially available hydrogen fluoride to form 1,3-dichloro-1,1,2-trifluoropropane.

$CFH_2CFClCF_2H$ (HCFC-244ba) may be prepared as follows. Commercially available 1,3-difluoro-2-propanol may be dehydrated to form 1,3-difluoro-1-propene which may then be dehydrohalogenated to form 3-fluoro-1-propyne. The 3-fluoro-1-propyne may then be fluorinated, chlorinated, and fluorinated to form 1,1,2,3-tetrafluoro-2-chloropropane.

$CFH_2CFHCF_2Cl$ (HCFC-244ec) may be prepared as follows. Commercially available 1,1,3-trichloropropene may be fluorinated to form 1,1-dichloro-3-fluoro-1-propene which may then be dehydrohalogenated to form 1-chloro-3-fluoro-1-propyne. The 1-chloro-3-fluoro-1-propyne may then be fluorinated to form 1-chloro-1,2,3-trifluoro-1-propene which may then be reacted with commercially available hydrogen fluoride to form 1-chloro-1,1,2,3-tetrafluoropropane.

$CFClHCH_2CF_3$ (HCFC-244fa) may be prepared as follows. Commercially available 1,1,3-trichloropropene may be fluorinated to form 1,1,1,2,3-pentafluoropropane. The 1,1,1,2,3-pentafluoropropane may then be dehydrohalogenated to form 1,3,3,3-tetrafluoro-1-propene which may then be reacted with commercially available hydrogen chloride to form 1-chloro-1,3,3,3-tetrafluoropropane.

$CF_2HCH_2CF_2Cl$ (HCFC-244fb) may be prepared as follows. Commercially available 2,2,3-tetrafluoro-1-propanol may be fluorinated to form 1,1,1,2,2,3-hexafluoropropane which may then be dehydrohalogenated to form 1,3,3-trifluoro-1-propyne. The 1,3,3-trifluoro-1-propyne may then be reacted with commercially available hydrogen chloride to form 1-chloro-1,3,3-trifluoro-1-propene which may then be reacted with commercially available hydrogen fluoride to form 1-chloro-1,1,3,3-tetrafluoropropane.

$CH_3CFClCF_2H$ (HCFC-253bb) may be prepared as follows. Commercially available 1,2-dibromopropane may be dehydrohalogenated to form propyne. The propyne may then be fluorinated, chlorinated, and fluorinated to form 2-chloro-1,1,2-trifluoropropane.

$CH_3CFHCF_2Cl$ (HCFC-253ec) may be prepared as follows. Commercially available 1,2-dichloropropane may be dehydrohalogenated to form 1-chloro-1-propene which may then be dehydrogenated to form 1-chloro-1propyne. The 1-chloro-1-propyne may then be reacted with commercially available hydrogen fluoride to form 1-chloro-1-fluoro-1-propene which may then be fluorinated to form 1-chloro-1,1,2-trifluoropropane.

The preferred straight chain hydrochlorofluorocarbons having 3 carbon atoms are $CF_2ClCFHCClH_2$, $CFH_2CFClCF_2H$, $CFH_2CFHCF_2Cl$, $CFClHCH_2CF_3$, $CF_2HCH_2CF_2Cl$, $CH_3CFClCF_2H$, and $CH_3CFHCF_2Cl$.

The straight chain hydrochlorofluorocarbons having 4 carbon atoms are listed in Table II below.

TABLE II

| Number | Chemical Formula |
| --- | --- |
| HCFC-354lbes | $CH_3CHFCClFCF_2Cl$ |
| HCFC-354lcd | $CH_3CClHCF_2CF_2Cl$ |
| HCFC-354mbd | $CH_3CClHCFClCF_3$ |
| HCFC-355lcf | $CFH_2CH_2CF_2CF_2Cl$ |
| HCFC-355lec | $CH_3CF_2CFHCF_2Cl$ |
| HCFC-355lef | $CF_2HCH_2CFHCF_2Cl$ |
| HCFC-355lff | $CF_3CH_2CH_2CF_2Cl$ |
| HCFC-355mbf | $CFH_2CH_2CFClCF_3$ |
| HCFC-355mcf | $CF_3CF_2CH_2CClH_2$ |
| HCFC-355mdc | $CH_3CF_2CClHCF_3$ |
| HCFC-355mdf | $CF_2HCH_2CClHCF_3$ |
| HCFC-355meb | $CH_3CFClCFHCF_3$ |
| HCFC-355med | $CFH_2CClHCFHCF_3$ |
| HCFC-355mfb | $CFH_2CFClCH_2CF_3$ |
| HCFC-355mfc | $CF_3CH_2CF_2CClH_2$ |
| HCFC-355mfd | $CF_2HCClHCH_2CF_3$ |
| HCFC-355mfe | $CFClHCFHCH_2CF_3$ |
| HCFC-355pcb | $CH_3CFClCF_2CF_2H$ |
| HCFC-355rcc | $CH_3CF_2CF_2CFClH$ |
| HCFC-364med | $CH_3CClHCFHCF_3$ |
| HCFC-364mff | $CFClHCH_2CH_2CF_3$ |
| HCFC-373lef | $CH_3CH_2CFHCF_2Cl$ |
| HCFC-373mfd | $CH_3CClHCH_2CF_3$ |
| HCFC-373mff | $CF_3CH_2CH_2CClH_2$ |
| HCFC-391rff | $CH_3CH_2CH_2CFClH$ |

TABLE II-continued

| Number | Chemical Formula |
|---|---|
| HCFC-391sbf | $CH_3CH_2CFClCH_3$ |

Known methods for making fluorinated compounds can be modified in order to form the straight chain hydrochlorofluorocarbons having 4 carbon atoms of the present invention.

For example, R. N. Haszeldine et al., "Addition of Free Radicals to Unsaturated Systems. Part XIII. Direction of Radical Addition to Chloro-1:1-difluoroethylene", *J. of Amer. Chem. Soc.*, 2193 (1957) teach the reaction of trifluoroiodomethane with chloro-1:1-difluoroethylene to prepare 3-chloro-1:1:1:2:2-pentafluoro-3-iodopropane which is then chlorinated to form 1,1-dichloro-2,2,3,3,3-pentafluoropropane (known in the art as HCFC-225ca). This known method can be modified to form $CF_3CF_2CH_2CClH_2$ (HCFC-355mcf) as follows. Commercially available perfluoroethyl iodide can be reacted with commercially available ethylene to prepare 1,1,1,2,2-pentafluoro-4-iodobutane which is then chlorinated to form 1,1,1,2,2-pentafluoro-4-chlorobutane.

$CH_3CF_2CFHCF_2Cl$ (HCFC-3551ec) may be prepared as follows. Commercially available 1,3-dichloro-2-butene may be fluorinated to form 1-chloro-2,3,3-trifluorobutane which may then be dehydrohalogenated to form 1-chloro-3,3-difluoro-1-butene. The 1-chloro-3,3-difluoro-1-butene may then be dehydrogenated to form 1-chloro-3,3-difluoro-1-propyne which may then be fluorinated to form 1-chloro-1,2,3,3-tetrafluoro-1-butene which may then be reacted with commercially available hydrogen fluoride to form 1-chloro-1,1,2,3,3-pentafluorobutane.

$CF_3CH_2CH_2CF_2Cl$ (HCFC-3551ff) may be prepared as follows. Commercially available 2,3-dichlorohexafluoro-2-butene may be dechlorinated to form hexafluoro-2-butyne. The hexafluoro-2-butyne may be hydrogenated to form 1,1,1,4,4,4-hexafluorobutane which may be chlorinated to form 1-chloro-1,1,4,4,4-pentafluorobutane.

$CFH_2CH_2CFClCF_3$ (HCFC-355mbf) may be prepared as follows. Commercially available 1,4-dichloro-2-butyne may be reacted with commercially available hydrogen fluoride to form 1,4-dichloro-2-fluoro-2-butene which may be fluorinated to form 1,2,4-trifluoro-2-butene. The 1,2,4-trifluoro-2-butene may be reacted with commercially available hydrogen chloride to form 2-chloro-1,2,4-trifluorobutane which may be dehydrohalogenated, fluorinated, dehydrohalogenated, and fluorinated to form 2-chloro-1,1,1,2,4-pentafluorobutane.

$CH_3CFCClHCF_3$ (HCFC-355mdc) may be prepared as follows. Commercially available 3,4-dichloro-1-butene may be dehydrogenated to form 3,4-dichloro-1-butyne which may be reacted with commercially available hydrogen fluoride to form 1,2-dichloro-3,3-difluorobutane. The 1,2-dichloro-3,3-difluorobutane may be dehydrogenated to form 1,2-dichloro-3,3-difluoro-1-butene which may be reacted with commercially available hydrogen fluoride to form 2-chloro-1,1,3,3-tetrafluorobutane. The 2-chloro-1,1,3,3-tetrafluorobutane may be dehydrogenated to form 2-chloro-1,1,3,3-tetrafluoro-1-butene which may be reacted with commercially available hydrogen fluoride to form 2-chloro-1,1,1,3,3-pentafluorobutane.

$CH_3CFClCFHCF_3$ (HCFC-355meb) may be prepared as follows. Commercially available 1,3-dichloro-2-butene may be fluorinated to form 2-chloro-2,3,4-trifluorobutane which may be dehydrohalogenated to form 3-chloro-1,3-difluoro-1-butene. The 3-chloro-1,3-difluoro-1-butene may be fluorinated to form 2-chloro-2,3,4,4-tetrafluorobutane which may be dehydrohalogenated to form 3-chloro-1,1,3-trifluoro-1-butene. The 3-chloro-1,1,3-trifluoro-1-butene may be fluorinated to form 2-chloro-2,3,4,4,4-pentafluorobutane.

$CH_3CFClCF_2CF_2H$ (HCFC-355pcb) may be prepared as follows. Commercially available 1,3-dichloro-2-butene may be fluorinated to form 2-chloro-2,3,4-trifluorobutane which may be dehydrogenated to form 3-chloro-1,2,3-trifluoro-1-butene. The 3-chloro-1,2,3-trifluoro-1-butene may be fluorinated to form 2-chloro-2,3,3,4,4-pentafluorobutane.

$CH_3CF_2CF_2CFClH$ (HCFC-355rcc) may be prepared as follows. Commercially available 1,3-dichloro-2-butene may be fluorinated to form 1-chloro-2,3,3-trifluorobutane which may be dehydrogenated to form 1-chloro-2,3,3-trifluoro-1-butene. The 1-chloro-2,3,3-trifluoro-1-butene may be fluorinated to form 1-chloro-1,2,2,3,3-pentafluorobutane.

$CH_3CClHCFHCF_3$ (HCFC-364med) may be prepared as follows. Commercially available 1,3-dichloro-2-butene may be reacted with commercially available hydrogen fluoride to form 1,3-dichloro-2-fluorobutane which may be dehydrohalogenated to form 1,3-dichloro-1-butene. The 1,3-dichloro-1-butene may be fluorinated to form 2-chloro-3,4,4-trifluorobutane which may be dehydrohalogenated to form 3-chloro-1,1-difluoro-1-butene. The 3-chloro-1,1-difluoro-1-butene may be fluorinated to form 2-chloro-3,4,4,4-tetrafluorobutane.

The preferred straight chain hydrochlorofluorocarbons having 4 carbon atoms are $CH_3CF_2CFHCF_2Cl$, $CF_3CH_2CH_2CF_2Cl$, $CFH_2CH_2CFClCF_3$, $CH_3CF_2CClHCF_3$, $CH_3CFClCFHCF_3$, $CH_3CFClCF_2CF_2H$, $CH_3CF_2CF_2CFClH$, and $CH_3CClHCFHCF_3$.

The branched chain hydrochlorofluorocarbons having 4 carbon atoms are listed in Table III below.

TABLE III

| Number | Chemical Formula |
|---|---|
| HCFC-345kms | $CH_3C(CF_3)FCFCl_2$ |
| HCFC-345lls | $CH_3C(CF_2Cl)FCF_2Cl$ |
| HCFC-355lms | $CH_3C(CF_3)HCF_2Cl$ |
| HCFC-355mop | $CF_2HC(CClH_2)HCF_3$ |
| HCFC-355mps | $CH_3C(CF_2H)ClCF_3$ |
| HCFC-355mrs | $CH_3C(CFClH)FCF_3$ |
| HCFC-373mss | $CH_3C(CH_3)ClCF_3$ |

Known methods for making fluorinated compounds can be modified in order to form the branched hydrochlorofluorocarbons having 4 carbon atoms of the present invention.

$CH_3C(CF_3)HCF_2Cl$ (HCFC-3551ms) may be prepared as follows. Commercially available 1-chloro-2-methylpropene may be fluorinated to form 1-chloro-1,2-difluoro-2-methylpropane which may be dehydrohalogenated to form 1-chloro-1-fluoro-2-methylpropene. The 1-chloro-1-fluoro-2-methylpropene may be fluorinated to form 1-chloro-1,1,2-trifluoro-2-methylpropane which may be dehydrohalogenated to form 3-chloro-3,3-difluoro-2-methylpropene. The 3-chloro-3,3-difluoro-2-methylpropene may be fluorinated to form 1-chloro-1,1,2,3-tetrafluoro-2-methylpropane which may be dehydrogenated to form 3-chloro-1,3,3-trifluoro-2-methylpropene. The 3-chloro-1,3,3-trifluoro-2-methylpropene may be fluorinated to form 1-chloro-1,1,2,3,3-pentafluoro-2-methylpropane which may be dehydrogenated to form 3-chloro-1,1,3,3-tetrafluoro-2-methylpropene. The 3-chloro-1,1,3,3-tetrafluoro-2-methylpropene may be fluorinated to form 1-chloro-1,1,3,3,3-pentafluoro-2-methylpropane.

$CH_3C(CF_2H)ClCF_3$ (HCFC-355mps) may be prepared as follows. Commercially available 1-chloro-2-methylpropene may be fluorinated to form 1,1,2-trifluoro-2-methylpropane which may be dehydrohalogenated to form 3,3-difluoro-2-methylpropene. The 3,3-difluoro-2-methylpropene may be fluorinated to form 1,1,2,3-tetrafluoro-2-methylpropane which may be dehydrohalogenated to form 1,3,3-trifluoro-2-methylpropene. The 1,3,3-trifluoro-2-methylpropene may be fluorinated to form 1,1,2,3,3-pentafluoro-2-methylpropane which may be dehydrohalogenated to form 1,1,3,3-tetrafluoro-2-methylpropene. The 1,1,3,3-tetrafluoro-2-methylpropene may be chlorinated to form 1,2-dichloro-1,1,4,4-tetrafluoro-2-methylpropane which may be fluorinated to form 2-chloro-1,1,1,3,3-pentafluoro-2-methylpropane.

$CH_3C(CFClH)FCF_3$ (HCFC-355mrs) may be prepared as follows. Commercially available 1-chloro-2-methylpropene may be fluorinated to form 1-chloro-1,2-difluoro-2-methylpropane which may be dehydrohalogenated to form 3-chloro-3-fluoro-2-methylpropene. The 3-chloro-3-fluoro-2-methylpropene may be fluorinated to form 1-chloro-1,2,3-trifluoro -2-methylpropane which may be dehydrohalogenated to form 3-chloro-1,3-difluoro-2-methylpropene. The 3-chloro-1,3-difluoro-2-methylpropene may be fluorinated to form 1-chloro-1,2,3,3-tetrafluoro-2-methylpropane which may be dehydrohalogenated to form 3-chloro-1,1,3-trifluoro -2-methylpropene. The 3-chloro-1,1,3-trifluoro-2-methylpropene may be fluorinated to form 1-chloro -1,2,3,3,3-pentafluoro-2-methylpropane.

The preferred branched hydrochlorofluorocarbons having 4 carbon atoms are $CH_3C(CF_3)HCF_2Cl$, $CH_3C(CF_2H)ClCF_3$, and $CH_3C(CFClH)FCF_3$.

The branched hydrochlorofluorocarbons having 5 carbon atoms are listed in Table IV below.

TABLE IV

| Number | Chemical Formula |
|---|---|
| HCFC-356mlfq | $CFH_2CH_2C(CF_2Cl)FCF_3$ |
| HCFC-357lcsp | $CF_2ClCF_2C(CH_3)FCF_2H$ |
| HCFC-357lmps | $CH_3C(CF_3)(CF_2H)CF_2Cl$ |
| HCFC-357lsem | $CF_3CFHC(CH_3)FCF_2Cl$ |
| HCFC-357mbsp | $CF_3CFClC(CH_3)FCF_2H$ |
| HCFC-357mcpo | $CF_3CF_2C(CF_2H)HCClH_2$ |
| HCFC-357mcsp | $CF_3CF_2C(CH_3)ClCF_2H$ |
| HCFC-357mcsr | $CF_3CF_2C(CH_3)FCFClH$ |
| HCFC-357mlcs | $CH_3CF_2C(CF_2Cl)HCF_3$ |
| HCFC-357mmbs | $CH_3CFClC(CF_3)HCF_3$ |
| HCFC-357mmel | $CF_2ClCHFC(CH_3)FCF_3$ |
| HCFC-357mmfo | $CH_2ClCH_2C(CF_3)FCF_3$ |
| HCFC-357mmfq | $CFH_2CH_2C(CF_3)ClCF_3$ |
| HCFC-357mmfr | $CFClHCH_2C(CF_3)HCF_3$ |
| HCFC-357mofm | $CF_3CH_2C(CClH_2)FCF_3$ |
| HCFC-357msem | $CF_3CFHC(CH_3)ClCF_3$ |
| HCFC-358mcsr | $CF_3CF_2C(CH_3)FCClFH$ |
| HCFC-366mmds | $CH_3CClHC(CF_3)HCF_3$ |
| HCFC-366mmfo | $CClH_2CH_2C(CF_3)HCF_3$ |
| HCFC-375lcss | $CF_2ClCF_2C(CH_3)FCH_3$ |
| HCFC-375mbss | $CF_3CFClC(CH_3)FCH_3$ |
| HCFC-393less | $CF_2ClCFHC(CH_3)HCH_3$ |
| HCFC-393mdss | $CF_3CClHC(CH_3)HCH_3$ |
| HCFC-393sfms | $CH_3CH_2C(CF_3)ClCH_3$ |
| HCFC-3-11-1rfss | $CFClHCH_2C(CH_3)HCH_3$ |

Known methods for making fluorinated compounds can be modified in order to form the branched hydrochlorofluorocarbons having 5 carbon atoms of the present invention.

$CFH_2CH_2C(CF_2Cl)FCF_3$ (HCFC-356mlfq) may be prepared as follows. Commercially available 1,4-dichloro-2-butene may be reacted with commercially available trifluoromethyl iodide to form 1,4-dichloro-2-trifluoromethyl-3-iodobutane which may be dehydrohalogenated to form 1,4-dichloro-3-trifluoromethyl-1-butene. The 1,4-dichloro-3-trifluoromethyl-1-butene may be hydrogenated to form 1,4-dichloro-2-trifluoromethylbutane which may be fluorinated to form 1-chloro-2-trifluoromethyl-4-fluorobutane. The 1-chloro-2-trifluoromethyl-4-fluorobutane may be dehydrogenated to form 1-chloro-2-trifluoromethyl-4-fluoro-1-butene which may be fluorinated to form 1-chloro-2-trifluoromethyl-1,2,4-trifluorobutane. The 1-chloro-2-trifluoromethyl-1,2,4-trifluorobutane may be dehydrohalogenated to form 1-chloro-2-trifluoromethyl-1,4-difluoro-1-butene which may be fluorinated to form 1-chloro-2-trifluoromethyl-1,1,2,4-tetrafluorobutane.

$CH_3C(CF_3)(CF_2H)CF_2Cl$ (HCFC-3571mps) may be prepared as follows. Commercially available 1,1-dichloropropene may be reacted with commercially available trifluoromethyl iodide to form 1,1-dichloro-1-iodo-2-trifluoromethylpropane which may be dehydrohalogenated to form 1,1-dichloro-2-trifluoromethyl-1-propene. The 1,1-dichloro-2-trifluoromethyl-1-propene may be hydrogenated to form 1,1-dichloro-2-trifluoromethylpropane which may be fluorinated to form 1,1-difluoro-2-trifluoromethylpropane. The 1,1-difluoro-2-trifluoromethylpropane may be dehydrogenated to form 1,1-difluoro-2-trifluoromethy-1-propene which may be reacted with commercially available trifluoromethyl iodide to form 1,1-difluoro-1-iodo-2,2-trifluoromethylpropane. The 1,1-difluoro-1-iodo-2,2-trifluoromethylpropane may be chlorinated to form 1-chloro-1,1-difluoro-2,2-trifluoromethylpropane which may be hydrogenated to form 1-chloro-1,1-difluoro-2-difluoromethyl-2-trifluoromethylpropane.

$CF_3CFHC(CH_3)FCF_2Cl$ (HCFC-3571sem) may be prepared as follows. Commercially available 1,4-dichloro-2-butene may be reacted with commercially available iodomethane to form 1,4-dichloro-3-iodo-2-methylbutane which may be dehydrohalogenated to form 1,4-dichloro-3-methyl-1-butene. The 1,4-dichloro-3-methyl-1-butene may be fluorinated to form 1-chloro-2-methyl-3,4,4-trifluorobutane which may be dehydrohalogenated to form 1,1-difluoro-3-methyl-4-chloro-1-butene. The 1,1-difluoro-3-methyl-4-chloro-1-butene may be fluorinated to form 1-chloro-2-methyl-3,4,4,4-tetrafluorobutane which may be dehydrogenated to form 1-chloro-2-methyl-3,4,4,4-tetrafluoro-1-butene. The 1-chloro-2-methyl-3,4,4,4-tetrafluoro-1-butene may be fluorinated to form 1-chloro-2-methyl-1,2,3,4,4,4-hexafluorobutane which may be dehydrohalogenated to form 1-chloro-2-methyl-1,3,4,4,4-pentafluoro-1-butene. The 1-chloro-2-methyl-1,3,4,4,4-pentafluoro-1-butene may be fluorinated to form 1-chloro-2-methyl-1,1,2,3,4,4,4-heptafluorobutane.

$CF_3CFClC(CH_3)FCF_2H$ (HCFC-357mbsp) may be prepared as follows. Commercially available 2,3-dichlorohexafluoro-2-butene may be reacted with commercially available iodomethane to form 2,3-dichloro-3-iodo-2-methyl-1,1,1,4,4,4-hexafluoropropane which may be fluorinated to form 2-methyl-3-chloro-1,1,1,2,3,4,4-heptafluorobutane. The 2-methyl-3-chloro-1,1,1,2,3,4,4-heptafluorobutane may be dehalogenated to form 3-chloro-2-methyl-1,1,3,4,4,4-hexafluoro-1-butene which may be reacted with commercially available hydrogen fluoride to form 3-chloro-2-methyl-1,1,2,3,4,4,4-heptafluorobutane.

$CF_3CF_2C(CH_3)ClCF_2H$ (HCFC-357mcsp) may be prepared as follows. Commercially available 2,3-dichlorohexafluoro-2-butene may be reacted with iodomethane to form 2-methyl-2,3-dichloro-3-iodo-1,1,1,4,4,4-hexafluorobutane which may be fluorinated to form 2-methyl-1,1,1,2,3,3,4,4,4-nonafluorobutane. The 2-methyl-1,1,1,2,3,3,4,4,4-nonafluorobutane may be dehalogenated to form 2-methyl-1,1,3,3,4,4,4-heptafluoro-1-butene which may be reacted with commercially available hydrogen chloride to form 2-chloro-2-methyl-1,1,3,3,4,4,4-heptafluorobutane.

$CH_3CF_2C(CF_2Cl)HCF_3$ (HCFC-357mlcs) may be prepared as follows. Commercially available 1,3-dichloro-2-butene may be reacted with commercially available trifluoromethyl iodide to form 1,3-dichloro-2-trifluoromethyl-3-iodobutane which may be fluorinated to form 1,3,3-trifluoro-2-trifluoromethylbutane. The 1,3,3-trifluoro-2-trifluoromethylbutane may be dehydrogenated to form 1,3,3-trifluoro-2-trifluoromethyl-1-butene which may be fluorinated to form 1,1,2,3,3-pentafluoro-2-trifluoromethylbutane. The 1,1,2,3,3-pentafluoro-2-trifluoromethylbutane may be dehydrohalogenated to form 1,1,3,3-tetrafluoro-2-trifluoromethyl-1-butene which may be reacted with commercially available hydrogen chloride to form 1-chloro-1,1,3,3-tetrafluoro-2-trifluoromethylbutane.

$CH_3CFClC(CF_3)HCF_3$ (HCFC-357mmbs) may be prepared as follows. Commercially available 2,3-dichlorohexafluoro-2-butene may be reacted with commercially available trifluoromethyl iodide to form 2,3-dichloro-3-iodo-2-trifluoromethyl-1,1,1,4,4,4-hexafluorobutane which may be fluorinated to form 2-trifluoromethyl-1,1,1,2,3,3,4,4,4-nonafluorobutane. The 2-trifluoromethyl-1,1,1,2,3,3,4,4,4-nonafluorobutane may be dehalogenated to form 3-trifluoromethyl-1,1,2,3,4,4,4-heptafluoro-1-butene which may be hydrogenated to form 2-trifluoromethyl-1,1,1,2,3,4,4-heptafluorobutane. The 2-trifluoromethyl-1,1,1,2,3,4,4-heptafluorobutane may be dehydrohalogenated to form 3-trifluoromethyl-1,2,3,4,4,4-hexafluoro-1-butene which may be hydrogenated to form 3-trifluoromethyl-1,2,3,4,4,4-hexafluorobutane. The 3-trifluoromethyl-1,2,3,4,4,4-hexafluorobutane may be dehydrohalogenated to form 3-trifluoromethyl-2,3,4,4,4-pentafluoro-1-butene which may be reacted with commercially available hydrogen chloride to form 3-chloro-2-trifluoromethyl-1,1,1,2,3-pentafluorobutane. The 3-chloro-2-trifluoromethyl-1,1,1,2,3-pentafluorobutane may be dehalogenated to form 3-chloro-2-trifluoromethyl-1,1,3-trifluoro-1-butene which may be reacted with commercially available hydrogen fluoride to form 3-chloro-2-trifluoromethyl-1,1,1,3-tetrafluorobutane.

$CF_2ClCHFC(CH_3)FCF_3$ (HCFC-357mmel) may be prepared as follows. Commercially available 2,3-dichlorohexafluoro-2-butene may be reacted with commercially available iodomethane to form 2,3-dichloro-3-iodo-1,1,1,4,4,4-hexafluoro-2-methylbutane which may be fluorinated to form 2-methylperfluorobutane. The 2-methylperfluorobutane may be dehalogenated to form 1,1,2,3,4,4,4-heptafluoro-3-methyl-1-butene which may be reacted with commercially available hydrogen chloride to form 4-chloro-1,1,1,2,3,4,4-heptafluoro-2-methylbutane.

The method of R. N. Haszeldine et al., supra, can be modified to form $CH_2ClCH_2C(CF_3)FCF_3$ (HCFC-357 mmfo) as follows. Commercially available perfluoroisopropyl iodide may be reacted with commercially available ethylene to prepare 2-trifluoromethyl-1,1,1,2-tetrafluoro-4-iodobutane which may then be chlorinated to form 2-trifluoromethyl-1,1,1,2-tetrafluoro-4-chlorobutane.

$CFH_2CH_2C(CF_3)ClCF_3$ (HCFC-357mmfq) may be prepared as follows. Commercially available 2,3-dichlorohexafluoro-2-butene may be reacted with commercially available trifluoromethyl iodide to form 2,3-dichloro-3-iodo-1,1,1,4,4,4-hexafluoro-2-trifluoromethylbutane which may be fluorinated to form 2-chloro-2-trifluoromethyl-perfluorobutane. The 2-chloro-2-trifluoromethyl-perfluorobutane may be dehalogenated to form 3-chloro-3-trifluoromethyl-1,1,2,4,4,4-hexafluoro-1-butene which may be hydrogenated to form 2-chloro-2-trifluoromethyl-1,1,1,3,4,4-hexafluorobutane. The 2-chloro-2-trifluoromethyl-1,1,1,3,4,4-hexafluorobutane may be fluorinated to form 3-chloro-3-trifluoromethyl-1,4,4,4-tetrafluoro-1-butene which may then be hydrogenated to form 2-chloro-2-trifluoromethyl-1,1,1,4-tetrafluorobutane.

$CF_3CFHC(CH_3)ClCF_3$ (HCFC-357msem) may be prepared as follows. Commercially available 2,3-dichlorohexafluoro-2-butene may be reacted with commercially available iodomethane to form 2,3-dichloro-3-iodo-1,1,1,4,4,4-hexafluoro-2-methylbutane which may be chlorinated to form 2,3,3-trichloro-1,1,4,4,4-hexafluoro-2-methylbutane. The 2,3,3-trichloro-1,1,1,4,4,4-hexafluoro-2-methylbutane may be dehalogenated to form 3-chloro-1,1,1,4,4,4-hexafluoro-2-methyl-2-butene which may be reacted with commercially available hydrogen fluoride to form 3-chloro-1,1,1,3,4,4,4-heptafluoro-2-methylbutane. The 3-chloro-1,1,1,3,4,4,4-heptafluoro-2-methylbutane may be dehydrohalogenated to form 1,1,1,4,4,4-hexafluoro-2-methyl-2-butene which may be reacted with commercially available hydrogen chloride to form 2-chloro-1,1,1,3,4,4,4-heptafluoro-2-methylbutane.

$CF_3CF_2C(CH_3)FCClFH$ (HCFC-358mcsr) may be prepared as follows. Commercially available 2,3-dichlorohexafluoro-2-butene may be reacted with commercially available trifluoromethyl iodide to form 2,3-dichloro-3-iodo-1,1,1,4,4,4-hexafluoro-2-methylbutane which may be fluorinated to form 2-methylperfluorobutane. The 2-methyl-perfluorobutane may be dehalogenated to form 2-methyl-perfluoro-1-butene which may be reacted with commercially available hydrogen fluoride to form 1,1,2,3,3,4,4,4-octafluoro-2-methylbutane. The 1,1,2,3,3,4,4,4-octafluoro-2-methylbutane may be dehalogenated to form 1,3,3,4,4,4-hexafluoro-2-methyl-1-butene which may be chlorinated to form 1,2-dichloro-1,3,3,4,4,4-hexafluoro-2-methylbutane. The 1,2-dichloro-1,3,3,4,4,4-hexafluoro-2-methylbutane may be dehydrohalogenated to form 1-chloro-1,3,3,4,4,4-hexafluoro-2-methyl-1-butene which may be reacted with commercially available hydrogen fluoride to form 1-chloro-1,2,3,3,4,4,4-heptafluoro-2-methylbutane.

$CH_3CClHC(CF_3)HCF_3$ (HCFC-366mmds) may be prepared as follows. Commercially available 2,3-dichlorohexafluoro-2-butene may be reacted with trifluoromethyl iodide to form 2,3-dichloro-3-iodo-1,1,1,4,4,4-hexafluoro-2-trifluoromethylbutane which may be chlorinated to form 3-iodo-1,1,1,4,4,4-hexafluoro-2-methyl-2-butene. The 3-iodo-1,1,1,4,4,4-hexafluoro-2-trifluoromethyl-2-butene may be hydrogenated to form 3-iodo-1,1,1,4,4,4-hexafluoro-2-trifluoromethylbutane which may be dehydrohalogenated to form 2-iodo-1,1,4,4,4-pentafluoro-3-trifluoromethyl-1-butene. The 2-iodo-1,1,4,4,4-pentafluoro-3-trifluoromethyl-1-butene may be hydrogenated to form 3-iodo-1,1,1,4,4,4-pentafluoro-2-trifluoromethylbutane which may be chlorinated to form 3-chloro-1,1,1,4,4-pentafluoro-2-trifluoromethylbutane. The 3-chloro-1,1,1,4,4-pentafluoro-2-trifluoromethylbutane may be dehydrohalogenated to form 2-chloro-1,4,4,4-tetrafluoro-3-trifluoromethyl-1-butene which may be hydrogenated to form 3-chloro-1,1,1,4-tetrafluoro-2-trifluoromethylbutane. The 3-chloro-1,1,1,4-tetrafluoro-2-trifluoromethylbutane may be dehydrohalogenated to form 2-chloro-4,4,4-trifluoro-3-trifluoromethyl-1-butene which may be hydrogenated to form 3-chloro-1,1,1-trifluoro-2-trifluoromethylbutane.

The preferred branched hydrochlorofluorocarbons having 5 carbon atoms are $CFH_2CH_2C(CF_2Cl)FCF_3$, $CH_3C(CF_3)(CF_2H)CF_2Cl$, $CF_3CFHC(CH_3)FCF_2Cl$, $CF_3CFClC(CH_3)FCF_2H$, $CF_3CF_2C(CH_3)ClCF_2H$, $CH_3CF_2C(CF_2Cl)HCF_3$, $CH_3CFClC(CF_3)HCF_3$, $CF_2ClCHFC(CH_3)FCF_3$, $CH_2ClCH_2C(CF_3)FCF_3$, $CFH_2CH_2C(CF_3)ClCF_3$, $CF_3CFHC(CH_3)ClCF_3$, $CF_3CF_2C(CH_3)FCClFH$, and $CH_3CClHC(CF_3)HCF_3$.

The present method is advantageous because the solvents have low atmospheric lifetimes.

Other advantages of the invention will become apparent from the following description.

DETAILED DESCRIPTION OF THE PREFERRED EMBODIMENTS

Known solvents may be blended with the solvents of the present method. Examples of useful known solvents are listed in Table V below.

TABLE V

| Number | Chemical Formula |
|---|---|
| HCFC-234cc | $CF_2ClCF_2CClH_2$ |
| HCFC-234cd | $CH_2FCF_2CFCl_2$ |
| HCFC-244ca | $CF_2HCF_2CClH_2$ |
| HCFC-244cb | $CFH_2CF_2CFClH$ |
| HCFC-253ca | $CFH_2CF_2CClH_2$ |
| HCFC-253cb | $CH_3CF_2CFClH$ |

HCFC-234cc may be formed by any known method such as the reaction of 1,1,1,2,2,3-hexachloropropane with antimony pentachloride and hydrogen fluoride at 100° C. HCFC-234cd may be formed by any known method such as the reaction of 1,1,1-trichloro-2,2,3-trifluoropropane with antimony pentachloride and hydrogen fluoride at 120° C.

HCFC-244ca may be formed by any known method such as the reaction of 1,1,2,2,3-pentachloropropane with antimony pentachloride and hydrogen fluoride at 100° C. HCFC-244cb may be formed by any known method such as the reaction of 1-chloro-1,1,2,2-tetrafluoropropane with cesium fluoride and tetrabutylammonium bromide at 150° C.

HCFC-253ca may be formed by any known method such as the reaction of 1,2,3-trichloro-2-fluoropropane with niobium pentachloride and hydrogen fluoride at 100° C. HCFC-253cb may be formed by any known method such as the reaction of 1,1,2,2-tetrachloropropane with tantalum pentafluoride and hydrogen fluoride at 130° C.

The present method removes most contaminants from the surface of a substrate. For example, the present method removes organic contaminants such as mineral oils from the surface of a substrate. Under the term "mineral oils", both petroleum-based and petroleum-derived oils are included. Lubricants such as engine oil, machine oil, and cutting oil are examples of petroleum-derived oils.

The present method also removes water from surface of a substrate. The method may be used in the single-stage or multi-stage drying of objects.

The present method may be used to clean the surface of inorganic substrates and some organic substrates. Examples of inorganic substrates include metallic substrates, ceramic substrates, and glass substrates. Examples of organic substrates include polymeric substrates such as polycarbonate, polystyrene, and acrylonitrile-butadiene-styrene. The method also may be used to clean the surface of natural fabrics such as cotton, silk, fur, suede, leather, linen, and wool. The method also may be used to clean the surface of synthetic fabrics such as polyester, rayon, acrylics, nylon, and blends thereof, and blends of synthetic and natural fabrics. It should also be understood that composites of the foregoing materials may be cleaned by the present method.

The present method may be used in vapor degreasing, solvent cleaning, cold cleaning, dewatering, and dry cleaning. In these uses, the object to be cleaned is immersed in one or more stages in the liquid and/or vaporized solvent or is sprayed with the liquid solvent. Elevated temperatures, ultrasonic energy, and/or agitation may be used to intensify the cleaning effect.

The present invention is more fully illustrated by the following non-limiting Examples.

EXAMPLES 1-85

Each solvent listed in Tables I through IV are added to mineral oil in a weight ratio of 50:50 at 27° C. Each solvent is miscible in the mineral oil.

Having described the invention in detail and by reference to preferred embodiments thereof, it will be apparent that modifications and variations are possible without departing from the scope of the invention defined in the appended claims.

What is claimed is:

1. A method of dissolving contaminants or removing contaminants from the surface of a substrate which comprises the step of:

using a solvent consisting essentially of a solvent selected from the group consisting of $CFH_2CCl_2CF_3$, $CF_3CFClCClH_2$, $CFH_2CFClCF_2Cl$, $CF_2ClCH_2CF_2Cl$, $CF_3CH_2CFCl_2$, $CH_3CFClCF_2H$, $CF_2ClCFHCClH_2$, $CFH_2CFClCF_2H$, $CF_2HCClHCF_2H$, $CF_2HCFHCFClH$, $CFH_2CFHCF_2Cl$, $CFClHCH_2CF_3$, $CF_2HCH_2CF_2Cl$, $CH_3CClHCF_2Cl$, $CF_2HCFHCClH_2$, $CH_3CFHCF_2Cl$, $CF_2HCH_2CFClH$, $CFH_2CH_2CF_2Cl$, CF₂HCH₂CClH₂, CH₃CFClCH₃, CH₃CH₂CFClH, and mixtures thereof to substantially dissolve or remove said contaminants.

2. The method of claim 1 wherein said solvent additionally comprises a solvent selected from the group consisting of CF₂ClCF₂CClH₂, CH₂FCF₂CFCl₂, CF₂HCF₂CClH₂, CFH₂CF₂CFClH, CFH₂CF₂CClH₂, CH₃CF₂CFClH, and mixtures thereof.

3. The method of claim 1 wherein said solvent is selected from the group consisting of CH₃CFClCF₂H, CF₂ClCFHCClH₂, CFH₂CFClCF₂H, CFH₂CFHCF₂Cl, CFClHCH₂CF₃, CF₂HCH₂CF₂Cl, CH₃CFHCF₂Cl, CF₃CH₂CClH₂, and mixtures thereof.

4. The method of claim 1 wherein said method removes organic contaminants from said surface.

5. The method of claim 1 wherein said method substantially removes contaminants from the surface of an organic substrate.

6. A method of dissolving contaminants or removing contaminants from the surface of a substrate which comprises the step of:
using a solvent consisting essentially of a solvent selected from the group consisting of CH₃CClHCF₂CF₂Cl, CH₃CHFCClFCF₂Cl, CH₃CClHCFClCF₃, CFH₂CH₂CF₂CF₂Cl, CH₃CF₂CFHCF₂Cl, CF₂HCH₂CFHCF₂Cl, CF₃CH₂CH₂CF₂Cl, CFH₂CH₂CFClCF₃, CF₃CF₂CH₂CClH₂, CH₃CF₂CClHCF₃, CF₂HCH₂CClHCF₃, CH₃CFClCFHCF₃, CFH₂CClHCFHCF₃, CFH₂CFClCH₂CF₃, CF₃CH₂CF₂CClH₂, CF₂HCClHCH₂CF₃, CFClHCFHCH₂CF₃, CH₃CFClCF₂CF₂H, CH₃CF₂CF₂CFClH, CH₃CClHCFHCF₃, CFClHCH₂CH₂CF₃, CH₃CH₂CFHCF₂Cl, CH₃CClHCH₂CF₃, CF₃CH₂CH₂CClH₂, CH₃CH₂CH₂CFClH, CH₃CH₂CFClCH₃, and mixtures thereof to substantially dissolve or remove said contaminants.

7. The method of claim 6 wherein said solvent additionally comprises a solvent selected from the group consisting of CF₂ClCF₂CClH₂, CH₂FCF₂CFCl₂, CF₂HCF₂CClH₂, CFH₂CF₂CFClH, CFH₂CF₂CClH₂, CH₃CF₂CFClH, and mixtures thereof.

8. The method of claim 6 wherein said solvent is selected from the group consisting of CH₃CF₂CFHCF₂Cl, CF₃CH₂CH₂CF₂Cl, CFH₂CH₂CFClCF₃, CH₃CF₂CClHCF₃, CH₃CFClCFHCF₃, CH₃CFClCF₂CF₂H, CH₃CF₂CF₂CFClH, CH₃CClHCFHCF₃, and mixtures thereof.

9. The method of claim 6 wherein said method removes organic contaminants from said surface.

10. The method of claim 6 wherein said method substantially removes contaminants from the surface of an organic substrate.

11. A method of dissolving contaminants or removing contaminants from the surface of a substrate which comprises the step of:
using a solvent consisting essentially of a solvent selected from the group consisting of CH₃C(CF₃)FCFCl₂, CH₃C(CF₂Cl)FCF₂Cl, CH₃C(CF₃)HCF₂Cl, CF₂HC(CClH₂)HCF₃, CH₃C(CF₂H)ClCF₃, CH₃C(CFClH)FCF₃, CH₃C(CH₃)ClCF₃ to substantially dissolve or remove said contaminants.

12. The method of claim 11 wherein said solvent additionally comprises a solvent selected from the group consisting of CF₂ClCF₂CClH₂, CH₂FCF₂CFCl₂, CF₂HCF₂CClH₂, CFH₂CF₂CFClH, CFH₂CF₂CClH₂, CH₃CF₂CFClH, and mixtures thereof.

13. The method of claim 11 wherein said solvent is selected from the group consisting of CH₃C(CF₃)HCF₂Cl, CH₃C(CF₂H)ClCF₃, CH₃C(CFClH)FCF₃, and mixtures thereof.

14. The method of claim 11 wherein said method removes organic contaminants from said surface.

15. The method of claim 11 wherein said method substantially removes contaminants from the surface of an organic substrate.

16. A method of dissolving contaminants or removing contaminants from the surface of a substrate which comprises the step of:
using a solvent consisting essentially of a solvent selected from the group consisting of CFH₂CH₂C(CF₂Cl)FCF₃, CF₂ClCF₂C(CH₃)FCF₂H, CH₃C(CF₃)(CF₂H)CF₂Cl, CF₃CFHC(CH₃)FCF₂Cl, CF₃CFClC(CH₃)FCF₂H, CF₃CF₂C(CF₂H)HCClH₂, CF₃CF₂C(CH₃)ClCF₂H, CF₃CF₂C(CH₃)FCFClH, CH₃CF₂C(CF₂Cl)HCF₃, CH₃CFClC(CF₃)HCF₃, CF₂ClCHFC(CH₃)FCF₃, CH₂ClCH₂C(CF₃)FCF₃, CFH₂CH₂C(CF₃)ClCF₃, CFClHCH₂C(CF₃)HCF₃, CF₃CH₂C(CClH₂)FCF₃, CF₃CFHC(CH₃)ClCF₃, CF₃CF₂C(CH₃)FCClFH, CH₃CClHC(CF₃)HCF₃, CClH₂CH₂C(CF₃)HCF₃, CF₂ClCF₂C(CH₃)FCH₃, CF₃CFClC(CH₃)FCH₃, CF₂ClCFHC(CH₃)HCH₃, CF₃CClHC(CH₃)HCH₃, CH₃CH₂C(CF₃)ClCH₃, CFClHCH₂C(CH₃)HCH₃, and mixtures thereof to substantially dissolve or remove said contaminants.

17. The method of claim 16 wherein said solvent additionally comprises a solvent selected from the group consisting of CF₂ClCF₂CClH₂, CH₂FCF₂CFCl₂, CF₂HCF₂CClH₂, CFH₂CF₂CFClH, CFH₂CF₂CClH₂, CH₃CF₂CFClH, and mixtures thereof.

18. The method of claim 16 wherein said solvent is selected from the group consisting of CFH₂CH₂C(CF₂Cl)FCF₃, CH₃C(CF₃)(CF₂H)CF₂Cl, CF₃CFHC(CH₃)FCF₂Cl, CF₃CFClC(CH₃)FCF₂H, CF₃CF₂C(CH₃)ClCF₂H, CH₃CF₂C(CF₂Cl)HCF₃, CH₃CFClC(CF₃)HCF₃, CF₂ClCHFC(CH₃)FCF₃, CH₂ClCH₂C(CF₃)FCF₃, CFH₂CH₂C(CF)Cl₃CF₃, CF₃CFHC(CH₃)ClCF₃, CF₃CF₂C(CH₃)FCClFH, and CH₃CClHC(CF₃)HCF₃.

19. The method of claim 16 wherein said method removes organic contaminants from said surface.

20. The method of claim 16 wherein said method substantially removes contaminants from the surface of an organic substrate.

* * * * *